United States Patent [19]

Battistini et al.

[11] Patent Number: 4,631,150

[45] Date of Patent: Dec. 23, 1986

[54] PROCESS FOR THE PREPARATION OF PENEMS

[75] Inventors: Carlo Battistini, Novate Milanese; Maurizio Foglio, Milan; Giovanni Franceschi, Milan; Cosimo Scarafile, Milan, all of Italy

[73] Assignee: Farmitalia Carlo Erba S.p.A., Milan, Italy

[21] Appl. No.: 637,878

[22] Filed: Aug. 6, 1984

[30] Foreign Application Priority Data

Aug. 11, 1983 [GB] United Kingdom ............... 8321677

[51] Int. Cl.$^4$ ................. C07D 499/00; A61K 31/425
[52] U.S. Cl. .................................... 540/310; 540/357; 514/210; 514/193; 514/195
[58] Field of Search ............... 260/245.2 R, 245.2 T; 514/210, 195, 193

[56] References Cited

U.S. PATENT DOCUMENTS

| | | |
|---|---|---|
| 4,443,373 | 4/1984 | Girijavallabhan et al. ... 260/245.2 R |
| 4,500,457 | 2/1985 | Gosteli et al. ............... 260/245.2 R |
| 4,584,133 | 4/1986 | Girijavallabhan ........... 260/245.2 R |

*Primary Examiner*—Nicholas S. Rizzo
*Attorney, Agent, or Firm*—Wegner & Bretschneider

[57] ABSTRACT

A process for preparing 2-methyl substituted penems useful as antibiotics agent and/or as intermediates thereof, by reacting an appropriate 1-imido-3,4-disubstituted azetidinone derivative with a trivalent organophosphorus compound in an inert solvent at a temperature of from 110° to 150° C. for a period of from 2 hours to a few days.

9 Claims, No Drawings

PROCESS FOR THE PREPARATION OF PENEMS

The present invention relates to a process for the preparation of 2-methyl substituted penems of the formula

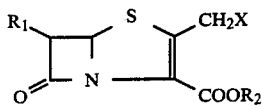

wherein
$R_1$ represents an organic group,
$R_2$ represents a hydrogen atom or a carboxy-protecting group, and
X represents
(i) an optionally protected hydroxy group,
(ii) a halogen atom,
(iii) an azido group,
(iv) an optionally substituted pyridyl group,
(v) a formyloxy group, an unsubstituted acyloxy having from 2 to 6 carbon atoms, or an acyloxy group having from 2 to 6 carbon atoms and being substituted by one or more halogen atoms, acyl groups having from 2 to 6 carbon atoms, amino, hydroxy, or mercapto groups, the amino, hydroxy or mercapto groups being free or protected,
(vi) a carbamoyloxy or N-alkyl-carbamoyloxy group,
(vii) an alkoxy or alkylthio group, each of which has from 1 to 12 carbon atoms and is unsubstituted or substituted by one or more halogen atoms, formyl groups, acyl groups having from 2 to 6 carbon atoms, amino, hydroxy, or mercapto groups, the amino, mercapto or hydroxy groups being free or protected,
(viii) a triarylmethylthio group, or
(ix) a heterocyclylthio group; and a pharmacuetically acceptable salt thereof.

The compounds of formula I are useful as antibiotics and/or as intermediates for the preparation of antibiotics by removing the O- and N-protecting groups or by converting the group X as defined above under (i) to (iii) into different X groups as defined above under (iv) to (ix).

The organic groups which $R_1$ may represent include optionally substituted aliphatic, cycloaliphatic, and aromatic hydrocarbon groups. The aliphatic hydrocarbon groups are preferably alkyl groups having from 1 to 12 carbon atoms. Methyl and ethyl groups, especially the latter, are particularly preferred. Preferred substituents, of which there may be one or more, are hydroxy, amino, cyano, and mercapto groups. Hydroxy, amino and mercapto substituents may be free or protected. The cycloaliphatic hydrocarbon groups are preferably monocycloalkyl groups having from 4 to 7 ring carbon atoms with the cyclohexyl group preferred. Preferred substituents, of which there may again be one or more, include in addition to those mentioned above, alkyl groups having from 1 to 6 carbon atoms, especially methyl and ethyl groups. The preferred aromatic hydrocarbon group is a phenyl group, which may be substituted by one or more of the substituents referred to in connection with the cycloaliphatic hydrocarbon groups. 1-Hydroxyethyl, free or protected, is an especially preferred value of $R_1$.

The carboxy protecting groups which $R_2$ may represent include
(a) alkyl groups having from 1 to 6 carbon atoms,
(b) haloalkyl groups having from 1 to 6 carbon atoms,
(c) alkenyl groups having from 2 to 4 carbon atoms,
(d) optionally substituted aryl groups,
(e) optionally substituted aralkyl groups, the alkyl part thereof having from 1 to 6 carbon atoms and
(f) aryloxyalkyl groups.
Examples of these are
(a) methyl, ethyl and t-butyl,
(b) 2,2,2-trichloroethyl,
(c) allyl,
(d) phenyl and p-nitrophenyl,
(e) benzyl, p-nitrobenzyl, p-methoxybenzyl, diphenylmethyl and di-(o-nitrophenyl)-methyl, and
(f) phenoxymethyl.

Other groups which should be mentioned as representative carboxy protecting groups are acetonyl, trimethylsilyl, diphenyl-t-butyl-silyl, and dimethyl-t-butyl-silyl. Also included are residues known to be hydrolyzed in vivo and having favorable pharmacokinetic properties, such as acetoxymethyl, pivaloyloxymethyl, and phthalidyl.

When X represents a protected hydroxy group, the preferred protecting groups are p-nitrobenzyloxycarbonyl, diphenyl-t-butyl silyl, trimethylsilyl, 2,2,2-trichloroethoxy-carbonyl, triphenylmethyl, and pyranyl.

When X represents a halogen atom, it preferably represents a chlorine, bromine, or iodine atom. When X represents an unsubstituted pyridyl group, it preferably represents 1-pyridyl. When X represents a substituted pyridyl group, it preferably represents 1-pyridyl substituted by a carbamoyl group, and particularly 4-carbamoyl. The acyloxy groups which X may represent are preferably aliphatic acyloxy groups having from 2 to 6 carbon atoms, in particular, acetyl. If X is an acyloxy group substituted by an acyl group, the acyl group is preferably an aliphatic acyl group having from 2 to 6 carbon atoms, in particular the acetyl group. When X represents an N-alkyl-carbamoyloxy group, the alkyl substituent preferably has from 1 to 6 carbon atoms and is most suitably a methyl or ethyl group. The alkoxy or alkylthio groups which X may represent preferably have from 1 to 6 carbon atoms. Methoxy, ethoxy, methylthio, and ethylthio groups are preferred. Triphenylmethylthio is the preferred triarylmethylthio group which X may represent.

When X represents a heterocyclylthio group, the heterocycle is preferably:
(A) a pentatomic or hexatomic heteromonocyclic ring, containing at least one double bond and at least one heteroatom selected from N, S, and O, unsubstituted or substituted by one or more substituents selected from:
(a) hydroxy, $C_1$–$C_6$ alkoxy, halogen, $C_2$–$C_6$ aliphatic acyl;
(b) $C_1$–$C_6$ alkyl unsubstituted or substituted by one or more substituents selected from hydroxy and halogen;
(c) $C_2$–$C_6$ alkenyl unsubstituted or substituted by one or more substituents selected from hydroxy and halogen;
(d) —S—$R_3$ wherein $R_3$ is hydrogen or $C_1$–$C_6$ alkyl; or —S—$CH_2$—$COOR_4$ wherein $R_4$ is hydrogen, $C_1$–$C_6$ alkyl, or a carboxy-protecting group;

(e) —$(CH_2)_m$—$COOR_4$ or —$CH=CH$—$COOR_4$ wherein m is zero, 1, 2, or 3 and $R_4$ is as defined above;

—$(CH_2)_m$—CN or —$(CH_2)_m$—$CONH_2$ wherein m is as defined above;

—$(CH_2)_m$—$SO_3H$ wherein m is as defined above or (f)

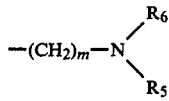

wherein m is as defined above, and each of $R_5$ and $R_6$, which may be the same or different, represents hydrogen, $C_1$-$C_6$ alkyl, or an aliphatic acyl group, or when one of $R_5$ and $R_6$ is hydrogen, the other may be also an amino protecting group; or (B) a heterobicyclic ring, containing at least two double bonds wherein each of the condensed heteromonocyclic rings, being the same or different, is a pentatomic or hexatomic heteromonocyclic ring containing at least one heteroatom selected from N, S, and O, said heterobicyclic ring being unsubstituted or substituted by one or more substituents selected from (a), (b), (c), (d), (e), and (f) as defined above.

In the above definitions of (A) and (B), preferred halogens are chlorine, bromine and iodine; preferred $C_1$-$C_6$ alkyl groups are methyl and ethyl; a preferred $C_2$-$C_6$ alkenyl group is allyl; a preferred aliphatic acyl group is acetyl; a carboxy protecting group may be any of the groups previously indicated for the $R_2$ substituent; and the free sulpho and carboxy groups possibly present may be salified, e.g. as sodium or potassium salts.

A heteromonocyclic ring of the above class (A) may be, for example, an optionally substituted thiazolyl, triazolyl, thiadiazolyl, tetrazolyl, or triazinyl ring. Preferred substituents on such rings are, for example, one or more substituents chosen from amino, hydroxy, oxo, and a $C_1$-$C_6$-alkyl group, preferably methyl or ethyl, wherein the $C_1$-$C_6$ alkyl group may be optionally substituted by a substituent chosen from carboxy, sulpho, cyano, carbamoyl, amino, methylamino, or dimethylamino.

A heterobicyclic ring of the above class (B) may be, for example, a tetrazolopyridazinyl radical optionally substituted by amino or carboxy.

In the above formula (I), the amino, hydroxy, a mercapto protecting groups possibly present may be those usually employed in the chemistry of penicillins and cephalosporins for this kind of function. They may be, for instance, optionally substituted, especially halo-substituted, acyl groups, e.g. acetyl, monochloroacetyl, dichloroacetyl, trifluoroacetyl, benzoyl, or p-bromophenacyl; triarylmethyl groups, in particular triphenylmethyl; silyl groups, in particular trimethylsilyl, dimethyl-t-butylsilyl, diphenyl-t-butyl-silyl; or also groups such as t-butoxycarbonyl, p-nitro-benzyloxycarbonyl, 2,2,2-trichloroethoxycarbonyl, benzyl, and when, in particular, the $R_1$ substituent in formula (I) is an alkyl group substituted by hydroxy, preferred protecting groups of the hydroxy function are p-nitrobenzyloxycarbonyl; dimethyl-t-butyl-silyl; diphenyl-t-butyl silyl; trimethylsilyl; 2,2,2-trichloroethoxycarbonyl; benzyl-p-bromo-phenacyl; triphenylmethyl, and pyranyl. All the alkyl and alkenyl groups, including the aliphatic hydrocarbon moiety of the alkoxy, alkylthio, and acyloxy groups, may be branched or straight chain.

A preferred aspect of this invention is directed to a process for preparing compounds of formula I wherein $R_1$ is

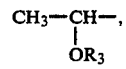

wherein $R_3$ is a hydrogen atom or a hydroxy protecting group, and

X represents an optionally protected hydroxy or a carbamoyloxy group. Particularly in the preparation of the foregoing compounds wherein $R_1$ is α-hydroxyethyl, X is carbamoyloxy and $R_2$ is acetoxymethyl.

The most preferred embodiment of the present invention is directed to the preparation of the compounds of the following formula (I'), having stereoconfiguration designated 5R,6S,/1(R)/and having the following representative spatial configuration:

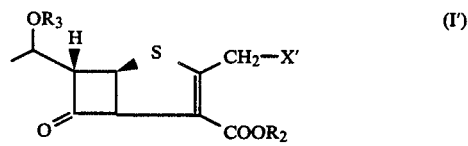

wherein $R_2$ and $R_3$ are as defined above and X' represents an optionally protected hydroxy or carbamoyloxy group.

The compounds of formula (I) are known antibacterial agents, being described, for example, in British Patent Specification No. 2,043,639 and in U.K. Patent Application Nos. 2097786-A and 2118181-A or, when X is as defined above under (i) to (iii), may be converted into useful antibiotics of formula (I) wherein X is as defined above under (iv) to (ix), as in detail explained and claimed in U.K. Patent Application Nos. 2111496-A and 2118181-A.

The present invention provides a process for the preparation of a penem having formula (I) as above defined, the process comprising reacting an azetidinone derivative having the formula

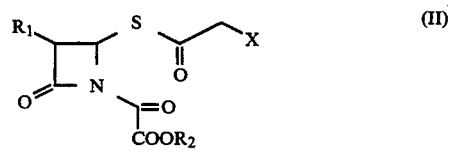

wherein $R_1$, $R_2$, and X are as above defined with up to 2 mole equivalents of a trivalent organophosphorus compound in an inert solvent at a temperature of from 110° to 150° C. for a period of from 2 hours to a few days.

The organophosphorus compound may be a cyclic or acyclic trialkylphosphite, triarylphosphite, mixed arylphosphite or phosphoramide. Trialkylphosphites, especially triethylphosphite, are preferred.

Suitable inert solvents include toluene, xylene, and dimethylformamide. Toluene and xylene are the preferred solvents. The reaction is preferably conducted at about 140° C. for from about 5 to about 15 hours.

Formula (II) encompasses all optical forms (racemic or optically active). The preferred configuration is 3S, 4R; particularly when $R_1$=hydroxyethyl, the (R) configuration is preferred for the carbon bearing the oxygen function, in order to obtain the preferred final (5R, 6S, 8R) stereochemistry of the penem nucleus.

The conversion of a compound of formula (I) wherein X is a protected hydroxy group into another compound of formula (I) wherein X is different may be carried out by known procedures, e.g. by removing the hydroxy protecting group on the 2-hydroxymethyl group and reacting the resultant compound of formula (I) wherein X is OH with trichloroacetylisocyanate.

The protecting groups present can be cleaved following well-known literature procedures, giving finally the free penem (I) as a salt (e.g. $R_2$=Na). The process according to the invention is a great improvement over prior art methods for obtaining penems of formula (I). The scheme hereinunder shows:
(1) The process described and claimed in British Patent Specification Nos. 2043639-B and 2111496-A (6 Steps: a–f);
(2) The process described and claimed in U.K. Patent Application No. 2111496-A (4 Steps: c–f); and
(3) The process of the present invention (Step i).

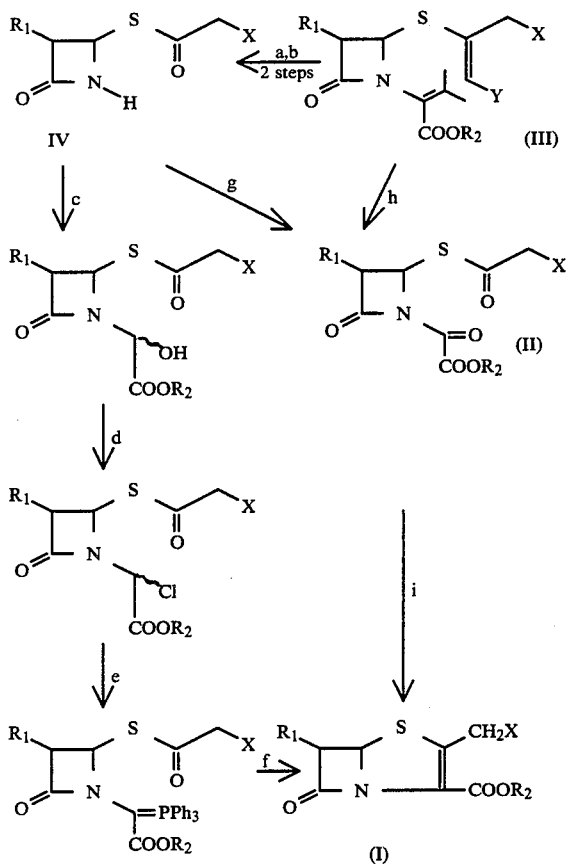

$R_1$, $R_2$, and X are as defined above and Y is as defined in the above cited prior art, including a hydrogen atom, an alkyl group having from 1 to 4 carbon atoms, cyano, alkoxycarbonyl, or a group of the formula $CH_2X$ where X is as defined above.

It is evident from the above scheme that the invention enables the penems of formula (I) to be obtained by a shorter route, avoiding some tedious steps, and with an obvious and highly desirable increase in yield. No changes in the stereochemical pattern were observed, maintaining also in this case the important feature of not forming diastereomeric mixtures. Since the number of steps required to make the compounds of formula (I) are reduced greatly, the yield of final product increases accordingly.

The starting material of the compounds of formula (II) may be prepared in various ways:
(1) By ozonolysis of compounds of formula (III), as shown in step (h) in the above scheme, and described in the above cited prior ary (Y represents a hydrogen atom or an alkyl, substituted alkyl, alkoxycarbonyl or cyano group);
(2) By ozonolysis of compounds of formula (V), prepared as described in Tetrahedron Letters, 24, pp. 1623–1629 (1983).

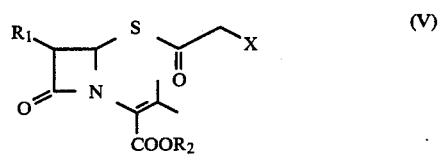

(3) From compounds of formula (IV), as shown in Step (g) in the above scheme; the compounds of formula (IV) can be obtained in different ways:

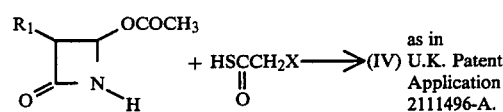

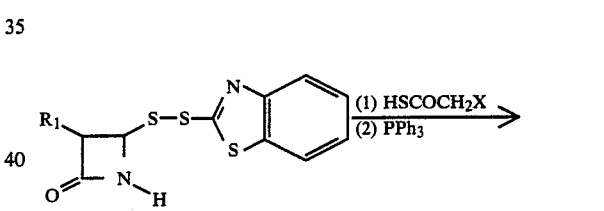

as in Tetrahedron
(IV) Letters, 24, pages
1627–1630 (1983).

as well as by other routes published in the literature. The compounds of formula (II) are then obtained by condensing the N—H free compound of formula (IV) with a suitable oxalyloyl derivative of formula (VI) wherein Z represents a halogen atom (preferably a chlorine, bromine or iodine atom)

following the literature procedure.
The following preparations and Examples illustrate the invention.

PREPARATION A

4β-Acetylglycoloylthio-3α-[1(R)-t-butyldimethyl-silyloxy-ethyl]-1-(p-nitrobenzyloxyoxalyl)-azetidin-2-one 4β-Acetoxymethylvinylthio-3α-[1(R)-t-butyl-dimethylsilyloxy-ethyl]-1-(1-p-nitrobenzyloxycarbonyl-2-methyl-1-propenyl)-azetidin-2-one (1.5 g) was dissolved in 80 ml of dichloromethane and cooled to −78° C. Ozone in oxygen was bubbled through the solution until a blue color appeared. The organic phase was diluted with ethyl acetate, washed with a saturated sodium metabisulphite solution, and then with water, and dried over anhydrous sodium sulphate.

I.R. 1820, 1780–1720 broad.

PREPARATION B

4β-t-Butyldiphenylsilylglycolloylthio-3α-[1(R)-t-butyldimethylsilyloxy-ethyl]-azetidin-2-one

Method A

3α-[1(R)-t-Butyldimethylsilyloxy-ethyl]-4-acetoxyazetidin-2-one (30 g) was dissolved in 80 ml of acetone and 45 ml of water. To this solution, 32 g of t-butyldiphenylsilyloxythioacetic acid dissolved in 80 ml of acetone and 100 ml of 1N sodium hydroxide were added at 0° C. After two hours, the precipitate was collected and washed with a cold acetone:water mixture. The title compound (18 g) was obtained as a white solid. M.p. 118°–122° C.

$[\alpha]_D^{-20}$ +90° (c=1.0, CHCl$_3$).

I.R. (CHCl$_3$) 4310, 1765, 1685, 1585, 1485, 1250, 1060 cm$^{-1}$.

P.M.R. (200 MHz, CDCl$_3$): 0.07 (s, 6H, Si (CH$_3$)$_2$); 0.88, 1.11 (two s, 18H SiC(CH$_3$)$_3$); 1.23 (d, J=5.5 Hz, 3H, CH$_3$CH); 3.24 (dd, J=2.5 Hz, 1H, H-6); 4.15–4.20 (m, 1H, CH$_3$CH); 4.24 (s, 2H, C=OCH$_2$O); 5.24 (d, J=2 Hz, 1H, H-5); 7.30–7.70 (m, 10H, Si(Ph)$_2$).

Method B

4β-Benzothiazolyldithio-3α-[1(R)-t-butyldimethylsilyloxyethyl]-azetidin-2-one (1.2 g) was dissolved in 30 ml of dichloromethane and 0.87 g of t-butyldiphenylsilyloxythioacetic acid were added thereto at room temperature. The crude reaction mixture was then treated with 0.74 g of triphenylphosphine and the title compound was purified by silica gel column chromatography to give 1.15 g of a product identical in all respects to the compound obtained by Method A.

PREPARATION C

4β-t-Butyldiphenylsilylglycolloylthio3α-[1(R)-t-butyldimethylsilyloxyethyl]-1-allyloxyoxalyl-azetidin-2-one 4β-t-Butyldiphenylsilylglycolloylthio-3α-[1(R)-t-butyldimethylsilyloxy-ethyl]-azetidin-2-one (1.37 g) was dissolved in 10 ml of dichloromethane and cooled to 10° C. Calcium carbonate (1 g), 0.445 g of allyloxyoxalyl chloride, and 0.54 ml of diisopropylethylamine dissolved in 2 ml of dichloromethane were added to the cooled solution. The reaction mixture was filtered, diluted with ethanol-free chloroform, and washed twice with iced water. The organic phase was dried over anhydrous sodium sulphate and evaporated. The crude product was used for the next step without further purification.

I.R. 1820, 1760, 1720.

PREPARATION D

4β-t-Butyldiphenylsilylglycolloythio-3α-[1(R)-t-butyldimethylsilyloxy-ethyl]-1-(1-p-nitrobenzyloxyoxalyl)-azetidin-2-one Starting from 4β-benzothiazolyldithio-3α-[1(R)-t-butyldimethylsilyloxyethyl]-1-(1-p-nitrobenzyloxycarbonyl-2-methyl-1-propenyl)-azetidin-2-one, operating as described in Preparation B, Method B, and ozonolysing the resultant compound according to the method described in Preparation A, the title compound was obtained.

PREPARATION E

4β-Glycolloylthio-3-α-[1(R)-t-butyldimethylsilyloxyethyl]-1-(1-p-nitrobenzyloxycarbonyl-2-methyl-1-propenyl)-azetidin-2-one Starting from 4β-benzothiazolyldithio-3α[1(R)-t-butyldimethylsilyloxy-ethyl]-1-(1-p-nitrobenzyloxycarbonyl-2-methyl-1-propenyl)-azetidin-2-one, and operating as described in preparation B, Method B, but using hydroxythioacetic acid instead of t-butyldiphenylsilyloxythioacetic acid, the title compound was obtained.

PREPARATION F

4β-Glycolloylthio-3-α-[1(R)-t-butyldimethylsilyloxyethyl]-1-(1-p-nitrobenzyloxyoxalyl)-2-azetidin-2-one

Method A

Starting from 4β-hydroxymethylvinylthio-3α-[1(R)-t-butyldimethylsilyloxy-ethyl]-1-(1-p-nitrobenzyloxycarbonyl-2-methyl-1-propenyl)-azetidin-2-one, and proceeding as described in Preparation A, the title compound was obtained.

Method B

Starting from 4β-glycolloylthio-3-α-[1(R)-t-butyldimethylsilyloxy-ethyl]-1-[1-p-nitrobenzyloxycarbonyl-2-methyl-1-propenyl]-azetidin-2-one, and proceeding as described in Preparation A, the title compound was obtained. It was identical in all respects to the compound obtained by Method A.

PREPARATION G

4β-[1-Methyl-1H-tetrazol-5-ylthioacetylthio-3α-]-[1(R)-t-butyldimethylsilyloxy-ethyl]-1-(p-nitrobenzyloxyoxalyl)-azetidin-2-one Starting from 4β-[(1-methyl-1H-tetrazol-5-ylthio)-methylvinylthio]-3α-[1(R)-t-butyldimethylsilyloxyethyl]-1-(1-p-nitrobenzyloxycarbonyl-2-methyl-1-propenyl)-azetidin-2-one, and proceeding as described in Preparation A, the title compound was obtained.

PREPARATION H

4β-Carbamoylglycolloylthio-3α-[1(R)-t-butyldimethylsilyloxy-ethyl]-1-(p-nitrobenzyloxyoxalyl)azetidin-2-one Starting from 4β-carbamoyloxymethylvinylthio-3α-[1(R)-t-butyldimethylsilyloxy-ethyl]-1-(1-p-nitrobenzyloxycarbonyl-2-methyl-1-propenyl)-azetidin-2-one, and proceeding as described in Preparation A, the title compound was obtained.

PREPARATION I

4β-Carbamoylglycolloylthio-3α-[1-(R)-trichloroethoxycarbonyloxyethyl]-1-(acetoxymethyloxyoxalyl)-azetidin-2-one 4β-(1-Carbamoyloxymethylvinyl)thio-3α-[1(R)-trichloroethoxycarbonyloxyethyl]-1-(1-acetoxymethyloxycarbonyl-2-methyl-1-propenyl)-azetidin-2-one (1.1 g) was dissolved in 30 ml of dichloromethane and cooled at −78° C. A flow of ozone in oxygen was then bubbled through the solution until the reaction was complete as indicated by TLC analysis.

Excess ozone was eliminated by a flow of nitrogen and the solution, at room temperature, was diluted with more dichloromethane and washed with an aqueous solution of sodium metabisulfite and then with brine.

The dried ($Na_2SO_4$) solution was evaporated giving 1 g of the crude title compound in the form of a white foam.

I.R. ($cm^{-1}$) 1825, 1770, 1730.

EXAMPLE 1 p-Nitrobenzyl(5R,6S)-2-acetoxymethyl-6-[1(R)-t-butyl-dimethylsiloxy-ethyl]-penem-3-carboxylate Crude 4β-acetylglycoloylthio-3α[1(R)-t-butyldimethylsilyloxyethyl]-1-(p-nitrobenzyloxyoxalyl)-azetidin-2-one (1.2 g), prepared as described in Preparation A, was dissolved in 60 ml of xylene. Triethylphosphite (1.5 ml) was added and the reaction mixture was refluxed for 12 hours. Purification of the reaction product by silica gel column chromatography gave 0.85 g of the title compound.

I.R.: 1795, 1755, 1720.

EXAMPLE 2 p-Nitrobenzyl(5R,6S)-2-acetoxymethyl-6-[1(R)-hydroxyethyl]-penem-3-carboxylate

Starting from p-nitrobenzyl(5R,6S)-2-acetoxymethyl-6-[1(R)-t-butyldimethylsilyloxy-ethyl]-penem-3-carboxylate, prepared as described in Example 1, and proceeding as described in Example 8 hereinafter, the title compound was obtained.

I.R.: 3500, 1790, 1755, 1715.

EXAMPLE 3

Sodium(5R,6S)-2-acetoxymethyl-6-[1(R)-hydroxyethyl]-penem-3-carboxylate p-Nitrobenzyl(5R,6S)-2-acetoxymethyl-6-[1(R)-hydroxyethyl]-penem-3-carboxylate (0.7 g), prepared as described in Example 2, was dissolved in 50 ml of ethyl acetate. A saturated aqueous sodium bicarbonate solution (30 ml) was added and the reaction mixture was shaken under hydrogen at room temperature. The crude aqueous phase was purified by reverse phase column chromatography giving 0.250 g of pure title compound.

PMP ($D_2O$): 1.31 (d, J=6, 5 Hz, 3H, $\underline{CH_3}$CH); 2.19 (s, 3H, OCO$\underline{CH_3}$); 3.92 (dd, J=1.5, 7.0 Hz, 1H, $\underline{H\text{-}6}$); 4.21 (m, 1H, CHOH); 5.10, 5.44 (d, J=14.0 Hz, 2H, $\underline{CH_2}$OCO); 5.67 (d, J=1.5 Hz, 1H, $\underline{H\text{-}5}$).

U.V. (ethanol 95%: $\lambda_{max}$ 262 nm (ε3410), 308 mm (ε4340).

EXAMPLE 4

Acetoxymethyl(5R,6S)-2-carbamoyloxy-methyl-6-[1(R)hydroxyethyl]penem-3-carboxylate

Step a

Acetoxymethyl(5R,6S)-2-carbamoyloxymethyl-6-[1(R)-trichloroethoxycarbonyloxyethyl]-penem-3-carboxylate Crude 4β-carbamoylglycolloylthio-3α-[1(R)-tricholoroethoxycarbonyloxyethyl]-1-(acetoxymethyloxyoxalyl)-azetidin-2-one (1 g, prepared as described in Preparation I) was dissolved in 25 ml of xylene; then 0.65 ml of triethylphosphite were added and the solution was refluxed for 4 hours.

Purification of the reaction product by silica gel chromatography gave 0.5 g of the title compound of this step.

$[\alpha]_D^{20} = +117°$ (c 1.00, $CHCl_3$).

UV $\lambda_{max}$ ($CHCl_3$) 324 nm.

IR $\nu_{max}$ (KBr) 1790, 1755, 1730, 1710.

PMR (60 MHz, $CDCl_3$) δ (p.p.m.); 1.53 (d, J=6.5 Hz, 3H, $\underline{CH_3}$ CH); 2.15 (s, 3H, CO$\underline{CH_3}$); 3.95 (dd, J=1.8, 8 Hz, 1H, $\underline{H\text{-}6}$); 4.77 (s, 2H, $\underline{CH_2}$$CCl_3$); 5.1 (m, 3H, $\underline{H\text{-}8}$, $\underline{NH_2}$; 5.08, 5.38 (two d, J=16 Hz, 2H $\underline{CH_2}$OCONH$_2$); 5.60 (d, J=1.8 Hz, 1H, $\underline{H\text{-}5}$; 5.8 (s, 2H, $\underline{CH_2}$OCOCH$_3$).

Step b

Acetoxymethyl(5R,6S)-2-carbamoyloxymethyl-6-[1(R)-hydroxyethyl]-penem-3-carboxylate (FCE 22891)

Acetoxymethyl(5R,6S)-2-carbamoyloxymethyl-6-[1(R)-trichloroethoxycarbonyloxyethyl]-penem-3-carboxylate (0.5 g) was dissolved in 5 ml of THF under nitrogen atmosphere and cooled to 0° C.

90% Aqueous acetic acid (1.5 ml) and a first portion of zinc dust (300 mg) were added. After two hours, a second portion of zinc dust (300 mg) was added and the mixture stirred for 4 hours more. The reaction mixture was filtered, the filtrate was diluted with ethylacetate, and washed with water, 3% aqueous $NaHCO_3$, and salt water.

Evaporation of the solvent gave 0.3 g of solid product. Crystallization from chloroform-hexane gave 0.27 g of pure title compound.

M.p. 127°–128° C.

$[\alpha]_D^{20} +137°$ (c 1.0, acetone).

UV $\lambda_{max}$ (EtOH 95%) (nm): 327 (ε 7500).

IR (KBr) $\nu_{max}$ ($cm^1$): 3500–3300, 1800, 1760, 1720, 1590

PMR (200 MHz, acetone-$d_6$), δ(ppm): 1.26 (d, J=6.0 Hz, 3H, $\underline{CH_3}$CH); 2.06 (s, 3H, CO$\underline{CH_3}$); 3.78 (s, 1H, O$\underline{H}$); 3.80 (dd, J=1.7, 6.4 Hz, 1H, $\underline{H\text{-}6}$); 4.14 (m, 1H, $CH_3\underline{CH}$), 5.08, 5.34 (two d, J=16.0 Hz, 2H, $\underline{CH_2}$O-CONH$_2$); 5.69 (d, J=1.7, 1H, $\underline{H\text{-}5}$); 5.80, 5.86 (two d, J=5.6 Hz, 2H, $CO_2\underline{CH_2}$OCO); 6.10 (bs, 2H, $\underline{NH_2}$).

EXAMPLE 5

Allyl(5R,6S)-2-t-butyldiphenylsilyloxymethyl-6-[1(R)-t-butyldimethylsilyloxy-ethyl]-penem-3-carboxylate 4β-t-Butyldiphenylsilylglycolloylthio-3α-[1(R)-t-butyldimethylsilyloxy-ethyl]-1-allyloxyoxalyl-azetidin-2-one (800 mg), prepared as described in Preparation C, was dissolved in 30 ml of xylene and refluxed. Triethyl phosphite (1.5 ml) dissolved in 2 ml of xylene was added and the mixture left refluxing for 5 hours. The title compound was purified by silica gel flash chromatography eluting with cyclohexane:ethyl acetate, giving 550 mg of pure product.

PMR (200 MHz, $CDCl_3$): 0.07 (s, 6H, Si($CH_3$)$_2$); 0.88 (s, 9H, Si($CH_3$)$_2$C($\underline{CH_3}$)$_3$); 1.06 (s, 9H, Si(Ph)$_2$C($\underline{CH_3}$)$_3$); 1.24 (d, J=6.2 Hz, 3H, $\underline{CH_3}$CH); 3.70 (dd, J=1.7, 4.8 Hz, 1H, $\underline{H\text{-}6}$); 4.23 (dq, J=4.8, 6.2 Hz, 1H, $CH_3\underline{CH}$); 4.55 (m, 2H, COO$\underline{CH_2}$); 4.86 (s, 2H, $\underline{CH_2}$OSi); 5.13, 5.26 (two dd, J=1.8, 9.17; Hz, 2H, =$\underline{CH_2}$); 5.55 (d, J=1.7 Hz, 1H, $\underline{H\text{-}5}$); 5.80 (m, 1H, $\underline{CH}$=$CH_2$); 7.4–7.7 (m, 10H, Si($\underline{Ph}$)$_2$).

EXAMPLE 6

Allyl(5R,6S)-2-hydroxymethyl-6-[1(R)-t-butyldimethylsilyloxyethyl]-penem-3-carboxylate Allyl(5R,6S)-2-t-butyldiphenylsilyloxymethyl-6-[1(R)-t-butyldimethylsilyloxy-ethyl]-penem-3-carboxylate (1.5 g), prepared as described in Example 5, was dissolved in 20 ml of tetrahydrofuran containing 3 ml of acetic acid and 1 g of tetrabutylammonium fluoride. The solution was left at room temperature for 15 minutes and then evaporated. The product was purified over silica gel, giving 0.6 g of the title compound.

$\lambda_{max}$ (CHCl$_3$) 326 nm.

$\nu_{max}$ (CHCl$_3$) 3600–3400, 1790, 1710, and 1580 cm$^{-1}$.

P.M.R. (CDCl$_3$) 0.13 (6H, s, C$\underline{H}_3$—Si), 0.93 (9H, s, tBu—Si), 1.30 (3H, d, J=7.0 Hz, C$\underline{H}_3$—CH), 3.76 (1H, dd, J=2 and 4.0 Hz, CH—C$\underline{H}$—CH), 3.82 (1H, C$\underline{H}_2$OH), 4.28 (1H, m, CH$_3$—C$\underline{H}$OSi—CH), 4.70 (4H, m, C$\underline{H}_2$OH + OC$\underline{H}_2$—CH=C$\underline{H}_2$); 5.28 (1H, d, J=10 Hz,

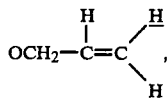

5.43 (1H, d, J=17 Hz,

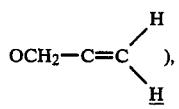

5.62 (1H, d, J=2 Hz, CH—C$\underline{H}$—S), 5.76–6.20 (1H, m OCH$_2$—C$\underline{H}$=CH$_2$).

EXAMPLE 7

Allyl(5R,6S)-2-(N-trichloroacetylcarbamoyloxymethyl)-6-[1(R)-t-butyldimethylsilyloxyethyl]-penem-3-carboxylate Allyl(5R,6S)-2-hydroxymethyl-6-/1(R)-t-butyldimethyl silyloxy-ethyl/-penem-3-carboxylate (3.1 g) prepared as described in Example 6, was dissolved in 100 ml of dichloromethane. The solution was cooled to −40° C. and 1.38 ml of trichloroacetyl isocyanate were added dropwise. The reaction mixture was raised to room temperature, and washed with a 2% aqueous solution of sodium bicarbonate and then with water. The washed reaction mixture was then dried over anhydrous sodium sulphate and evaporated to give 4.8 g of a white wax, which was used for the next step without further purification.

EXAMPLE 8

Allyl(5R,6S)-2-carbamoyloxymethyl-6-[1(R)-hydroxyethyl]-penem-3-carboxylate

Crude allyl(5R,6S)-2-(N-trichloroacetylcarbamoyloxymethyl-6-[1(R)-t-butyldimethylsilyloxyethyl]-penem-3-carboxylate (4.8 g), prepared as described in Example 7, was dissolved in 40 ml of tetrahydrofuran. Acetic acid (4.43 ml) and 7.35 g of tetrabutylammonium fluoride were added at room temperature. The reaction mixture was left for 24 hours under nitrogen. The solvent was then evaporated off and the residue was dissolved in 100 ml of ethyl acetate. The resultant solution was washed first with a saturated solution of sodium bicarbonate. The washed solution was then dried over anhydrous sodium sulphate and evaporated to a small volume. The product was precipitated by addition of toluene. There were obtained 1.56 g of a white solid.

$\lambda_{max}$ (CHCl$_3$) 322 nm.

$\nu_{max}$ (KBr) 3650–3150, 1775, 1725 and 1700 cm$^{-1}$.

P.M.R. (CDCl$_3$+DMSO-d$_6$) 1.26 (3H, d, J=6.0 Hz, C$\underline{H}_3$—CH), 3.68 (1H, dd, J=2 and 7.0 Hz, OCH—C$\underline{H}$—CHS), 4.07 (1H, m, CH$_3$—CHOH—CH), 4.64 (2H, m, COOC$\underline{H}_2$—CH=CH$_2$), 5.07 (1H, s, CH$_3$—CHOH—CH), 5.24 (2H, ABq, J=16 Hz, C$\underline{H}_2$O-CONH$_2$); 5.20 (1H, d, J=12 Hz,

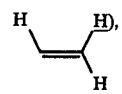

5.36 (1H, d, J=19 Hz

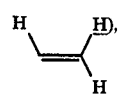

5.63 (1H, d, J=2 Hz, CH—C$\underline{H}$—S), 5.60–6.10 (1H, m, COOCH$_2$—C$\underline{H}$=CH$_2$), 6.06 (2H, CON$\underline{H}_2$).

EXAMPLE 9

Sodium(5R,6S)-2-carbamoyloxymethyl-6-[1(R)-hydroxyethyl]-penem-3-carboxylate

Allyl(5R,6S)-2-carbamoyloxymethyl-6-[1(R)-hydroxyethyl]-penem-3-carboxylate (1.56 g), prepared as described in Example 8, was dissolved in 20 ml of tetrahydrofuran and treated with 0.15 g of triphenylphosphine, 1.29 g of sodium ethylhexanote, and 0.15 g of tetrakistriphenylphosphine-Pd at room temperature. A solid precipitated, and was collected after 30 minutes by centrifugation, purified over Lichroprep RP-18 (Merck), and finally lyophilized. A white lyophilized compound in a quantity of 1.34 g was obtained.

P.M.R. (D$_2$O): 1.31 (d, J=6.5 Hz, 3H, C$\underline{H}_3$CH); 3.91 (dd, J=1.5, 6.0 Hz, 1H, $\underline{H}$-6); 4.25 (m, 1H, C$\underline{H}$OH); 5.02 and 5.36 (two d, 2H C$\underline{H}_2$OCO); 5.66 (d, J=1.5 Hz, 1H, $\underline{H}$-5).

UV $\lambda_{max}$ (H$_2$O) 258 (3200), 308 (5780) nm.

[α]$_D^{20}$ +143° (c=0.97 H$_2$O).

EXAMPLE 10 p-Nitrobenzyl(5R,6S)-2-hydroxymethyl-6-[1(R)-t-butyldimethylsilyloxy-ethyl]-penem-3-carboxylate Starting from 4β-glycolloylthio-3α-[1(R)-t-butyldimethylsilyloxy-ethyl]-1-(p-nitrobenzyloxyoxalyl)-azetidin-2-one, prepared as described in Preparation F, and proceeding as described in Example 1, the title compound was obtained.

PMR (CDCl$_3$) 0.05 (6H, s, SiMe$_2$); 0.85 (9H, s, SiBu$^t$) 1.25 (3H, d, C$\underline{H}_3$—CH); 3.44 (1H, t, CH$_2$O$\underline{H}$) 3.78 (1H, dd, OCH—C$\underline{H}$—CHS); 4.29 (1H, m, CH$_3$—CHOSi—CH); 4.64 (2H, d, C$\underline{H}_2$OH); 5.32 (2H, ABq, O—C$\underline{H}$ $_2$Ar); 5.64 (1H, d, CH—C$\underline{H}$—S), 7.60 and 8.20 (2H each, d, Ar).

EXAMPLE 11 p-Nitrobenzyl(5R,6S)-2-(N-trichloroacetylcarbamoyloxymethyl)-6-[1(R)-t-butyldimethylsilyloxyethyl]-penem-3-carboxylate Starting from p-nitrobenzyl(5R,6S)-2-hydroxymethyl-6-[1(R)-t-butyldimethylsilyloxy-ethyl]-penem-3-carboxylate, prepared as described in Example 10, and following the procedure described in Example 7 the title compound was obtained.

$\lambda_{max}$ (CHCl$_3$) 265 (10668), 328 (6575) nm.
$\nu_{max}$ (nujol) 1800–1790, 1745, 1720–1710 cm$^{-1}$.
PMR (CDCl$_3$) 0.04 and 0.09 (3H each, s, SiMe$_2$), 0.82 (9H, s, SiBu$^t$), 1.24 (3H, d, J=7 Hz; $\underline{CH_3}$—CH), 3.79 (1H, dd, J=1.8 and 4.0 Hz, OCH—$\underline{CH}$—CHS), 4.25 (1H, m, CH$_3$—CHOSi—CH), 5.30 (2$\overline{H}$, ABq, J=13.5 Hz, O—$\underline{CH_2}$—$\overline{Ar}$), 5.47 (2H, ABq, J=14.5 Hz, $\underline{CH_2}$O); 5.67 (1$\overline{H}$, d, J=1.8 Hz, CH—$\underline{CH}$—S); 7.6 ($\overline{1H}$, bs, CO—NH—CO); 7.60 and 8.17 ($\overline{2H}$ each, d, J=8 Hz, Ar).

EXAMPLE 12 p-Nitrobenzyl(5R,6S)-2-carbamoyloxymethyl-6-[1(R)-hydroxyethyl]-penem-3-carboxylate Starting from p-nitrobenzyl(5R,6S)-2-(N-trichloroacetylcarbamoyloxymethyl)-6-[1(R)-t-butyl-dimethylsilyloxy-methyl]-penem-3-carboxylate, prepared as described in Example 11, and following the procedure described in Example 8, the title compound was obtained.

$\lambda_{max}$ (EtOH 95%) 265, 324 nm,
$\nu_{max}$ (CH$_2$Cl$_2$) 3600–3400, 1790, 1740 and 1715 cm$^{-1}$.
PMR (acetone-d$_6$) 1.30 (d, 3H, J=6.0 Hz, CH$_3$—CH); 3.84 (1H, dd, J=1.8, 6.5 Hz, OCH—$\overline{CH}$—CHS); 4.2 (2H, m, CH$_3$—CHOH—CH), 5.24 (2H, $\overline{ABq}$, J=15.5 Hz, $\underline{CH_2}$—OCO$\underline{NH_2}$); 5.43 (2H, ABq, J=13.5 Hz, O—$\overline{CH_2}$—Ar), 5.72 (1H, d, J=1.8 Hz, CH—$\underline{CH}$—S); 6.$\overline{10}$ (2H, br s, CO$\underline{NH_2}$); 7.74 and 8.21 (2H each, d, J=8 Hz, Ar).

EXAMPLE 13

Sodium(5R,6S)-2-carbamoyloxymethyl-6-[1(R)-hydroxyethyl]-penem-3-carboxylate

Starting from p-nitrobenzyl(5R,6S)-2-carbamoyloxymethyl-6-[1(R)-hydroxyethyl]-penem-3-carboxylate, prepared as described in Example 12, and proceeding as shown in Example 3, the title compound was obtained, spectroscopic data were as given in Example 9.

EXAMPLE 14 p-Nitrobenzyl(5R,6S)-2-[(1-methyl-1H-tetrazol-5-ylthio)-methyl]-6-[1(R)-t-butyldimethylsilyloxy-ethyl]-penem-3-carboxylate Starting from 4β-[1-methyl-1H-tetrazol-5-ylthioacetylthio)-3α-[1(R)-t-butyldimethylsilyloxy-ethyl]-1-(p-nitrobenzyloxyoxalyl)-azetidin-2-one, prepared as described in Preparation G, and proceeding as described in Example 1, the title compound was obtained.

EXAMPLE 15 p-Nitrobenzyl(5R,6S)-2-[(1-methyl-1H-tetrazol-5-ylthio)-methyl]-6-[1(R)-hydroxyethyl]-penem-3-carboxylate Starting from p-nitrobenzyl(5R,6S)-2-[(1-methyl-1H-tetrazol-5-ylthio)-methyl]-6-[1(R)-t-butyldimethylsilyloxy-ethyl]-penem-3-carboxylate, prepared as described in Example 14, and proceeding as described in Example 8, the title compound was obtained.

EXAMPLE 16

Sodium(5R,6S)-2-[(1-methyl-1H-tetrazol-5-ylthio)-methyl]-6-[1(R)-hydroxyethyl]-penem-3-carboxylate p-Nitrobenzyl(5R,6S)-2-[(1-methyl-1H-tetrazol-5-ylthio)-methyl]-6-[1(R)-hydroxyethyl]-penem-3-carboxylate (0.7 g), prepared as described in Example 15, was dissolved in 40 ml of tetrahydrofuran and cooled to 0° C. An aqueous solution of ammonium chloride was added together with iron dust. When the reaction was complete, the insoluble material was filtered off and the product purified by reverse phase column chromatography. The title compound was obtained in a quantity of 0.28 g.

PMR (D$_2$O): 1.28 (3H, d, J=6.3 Hz); 3.87 (1H, dd, J=1.4 and 6.3 Hz); 4.10 (3H, s); 4.19 (1H, m); 4.40 (2H, ABq, J=16.0 Hz, separation of inner lines=13 Hz); 5.59 (1H, d, J=1.4 Hz).

EXAMPLE 17 p-Nitrobenzyl(5R,6S)-2-carbamoyloxymethyl-6-[1(R)-t-butyl-dimethylsilyloxy-ethyl]-penem-3-carboxylate Starting from 4β-carbamoylglycolloylthio-3α-[1(R)-t-butyldimethylsilyloxy-ethyl]-1-(p-nitrobenzyloxyoxalyl)-azetidin-2-one, prepared as described in Preparation H, and proceeding as described in Example 1, the title compound was obtained.

EXAMPLE 18 p-Nitrobenzyl(5R,6S)-2-carbamoyloxymethyl-6-[1(R)-hydroxyethyl]-penem-3-carboxylate Starting from p-nitrobenzyl(5R,6S)-2-carbamoyloxymethyl-6-[1(R)-t-butyldimethylsilyloxy-ethyl]-penem-3-carboxylate, prepared as described in Example 17, and proceeding as described in Example 8, the title compound was obtained. Spectroscopic data were as given in Example 12.

What is claimed is:

1. A process for the preparation of a compound of the formula:

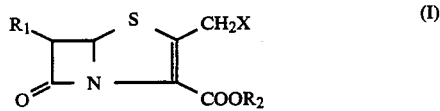

wherein

R$_1$ represents an organic group selected from the group consisting of a C$_1$ to C$_{12}$ aliphatic hydrocarbon group, a substituted C$_1$ to C$_{12}$ aliphatic hydrocarbon group substituted with at least one of hydroxy, amino, cyano, or mercapto; a C$_4$ to C$_7$ monocycloalkyl group, a substituted C$_4$ to C$_7$ monocycloalkyl group substituted with at least one of hydroxy, amino, cyano, mercapto, or C$_1$ to C$_6$ alkyl; phenyl; and substituted phenyl substituted with at least one of hydroxy, amino, cyano, mercapto, or C$_1$ to C$_6$ alkyl, R$_2$ represents a hydrogen atom or a carboxy-protecting group, and X represents:
 (i) an optionally-protected hydroxy group,
 (ii) a halogen atom,
 (iii) an azido group, (iv) a pyridyl group which is unsubstituted or substituted by carbamoyl groups,
(v) a formyloxy group, an unsubstituted acyloxy group having from 2 to 6 carbon atoms, or an acyloxy group having from 2 to 6 carbon atoms, being substituted by one or more halogen atoms, acyl groups having from 2 to 6 carbon atoms, amino, hydroxy, or mercapto groups, the amino, hydroxy or mercapto groups being free or protected,
(vi) a carbamoyloxy or N-alkyl-carbamoyloxy group,
(vii) an alkoxy or alkylthio group, each of which has from 1 to 12 carbon atoms and is unsubstituted or substituted by one or more halogen atoms, formyl groups, acyl groups having from 2 to 6 carbon atoms, amino, hydroxy, or mercapto groups, the amino, mercapto, or hydroxy groups being free or protected,
(viii) a triarylmethylthio group, or
(ix) a heterocyclylthio group, wherein the heterocycle is a pentatomic or hexatomic heteromonocyclic ring, containing at least one double bond and at least one heteroatom selected from N, S, and O, unsubstituted or substituted by one or more substituents or a heterobicyclic ring, containing at least two double bonds wherein each of the condensed heteromonocyclic rings, being the same or different, is a pentatomic or hexatomic heteromonocyclic ring containing at least one heteroatom selected from N, S, and O, said heterobicyclic ring being unsubstituted or substituted by one or more substituents,
which comprises the steps of reacting an azetidinone derivative of the formula

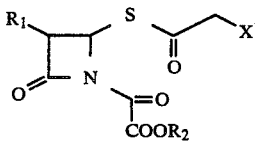

(II)

wherein $R_1$, $R_2$, and X are as above defined
with up to 2 mole equivalents of a trivalent organophosphorous compound wherein said organophosphorous compound is selected from the group consisting of a cyclic trialkylphosphite, and acyclic-trialkylphosphite, a triarylphosphite, a mixed arylphosphite, and phosphoramide
in an inert solvent
at a temperature of from 110° to 150° C. for a period of at least 2 hours or more.

2. The process of claim 1 wherein the temperature is about 140° C. and the period is from 5 to 15 hours.

3. The process of claim 1 wherein said inert solvent is selected from the group consisting of toluene, xylene, and dimethylformamide.

4. The process of claim 1, wherein said inert solvent is xylene, said organophosphorus compound is triethylphosphite, and said process is carried out at about 140° for a period of from 5 to 15 hours.

5. The process of claim 4, wherein said azetidinone derivative is a compound of the formula

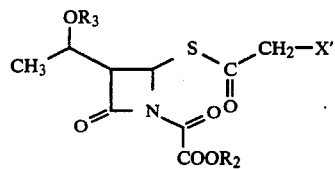

(II')

wherein $R_2$ is a hydrogen atom or a carboxy-protecting group, $R_3$ is a hydrogen atom or a hydroxy-protecting group, and X' represents an optionally protected hydroxy or carbamoyloxy group, resulting in the production of a compound of the formula

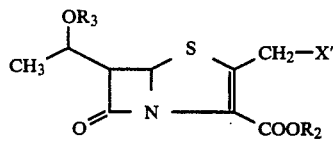

(X')

wherein $R_2$, $R_3$ and X' are as above defined.

6. The process of claim 5 wherein said azetidinone derivative is 4β-t-butyldiphenylsilylglycolloylthio-3-α-[1(R)-t-butyldimethylsilyloxyethyl]-1-allyloxyoxalyl-azetidin-2-one, resulting in the production of allyl(5R,6S)-2-t-butyldiphenylsilyloxymethyl-6-[1(R)-t-butyldimethylsilyloxyethyl]-penem-3-carboxylate.

7. The process of claim 5 wherein said azetidinone derivative is 4β-carbamoylglycolloylthio-3-α-[1(R)-trichloroethoxycarbonyloxyethyl]-1-(acetoxymethyloxyoxalyl)-azetidin-2-one, resulting in the production of acetoxymethyl(5R,6S)-2-carbamoyloxymethyl-6-[1(R)-trichloroethoxycarbonyloxyethyl]-penem-3-carboxylate.

8. The process of claim 1 wherein $R_2$ is selected from the group consisting of methyl, ethyl, t-butyl, 2,2,2-trichloroethyl, allyl, phenyl, p-nitrophenyl, benzyl, p-nitrobenzyl, p-methoxybenzyl, diphenylmethyl, di-(o-nitrophenyl)-methyl, phenoxymethyl, acetonyl, trimethylsilyl, diphenyl-t-butylsilyl, dimethyl-t-butylsilyl, acetoxymethyl, pivaloyloxymethyl, phthalidyl, p-nitrobenzyloxycarbonyl, 2,2,2-trichloroethoxy-carbonyl, triphenylmethyl, and pyranyl.

9. The process of claim 1 wherein said heterocyclylthio ring being substituted by one or more substituents selected from
(a) hydroxy, $C_1$–$C_6$ alkoxy, halogen, $C_2$–$C_6$ aliphatic acyl;
(b) $C_1$–$C_6$ alkyl unsubstituted or substituted by one or more substituents selected from hydroxy and halogen;
(c) $C_2$–$C_6$ alkenyl unsubstituted or substituted by one or more substituents selected from hydroxy and halogen;
(d) —S—$R_3$ wherein $R_3$ is hydrogen or $C_1$–$C_6$ alkyl; or —SCH$_2$— COOR$_4$ wherein $R_4$ is hydrogen, $C_1$–$C_6$ alkyl, or a carboxy-protecting group; and
(e) —(CH$_2$)$_m$—COOR$_4$ or —CH=CH—COOR$_4$ wherein m is zero, 1, 2, or 3 and $R_4$ is as defined above; —(CH$_2$)$_m$—CN or —(CH$_2$)$_m$—CONH$_2$ wherein m is as defined above; —(CH$_2$)$_m$—SO$_3$H wherein m is as defined above or $R_6$
(f) —(CH$_2$)$_m$—N wherein m is as defined above, $R_5$ and each of $R_5$ and $R_6$, which may be the same or different, represents hydrogen, $C_1$–$C_6$ alkyl, or an aliphatic acyl group, or when one of $R_5$ and $R_6$ is hydrogen, and other may be also an amino protecting group.

* * * * *